United States Patent
Schmidt et al.

(10) Patent No.: US 10,653,345 B2
(45) Date of Patent: May 19, 2020

(54) BLOOD PROCESSING APPARATUS COMPRISING A HOLDER DEVICE FOR A MEASUREMENT DEVICE

(71) Applicant: Fresenius Kabi Deutschland GmbH, Bad Homburg (DE)

(72) Inventors: Frank Schmidt, Schiffweiler (DE); Ilka Sternheimer, Frankfurt (DE); Artur Meisberger, St. Wendel (DE); Lars Michel, Rosbach v.d.H. (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 474 days.

(21) Appl. No.: 15/503,152

(22) PCT Filed: Aug. 3, 2015

(86) PCT No.: PCT/EP2015/067813
§ 371 (c)(1),
(2) Date: Feb. 10, 2017

(87) PCT Pub. No.: WO2016/030147
PCT Pub. Date: Mar. 3, 2016

(65) Prior Publication Data
US 2017/0227438 A1    Aug. 10, 2017

(30) Foreign Application Priority Data

Aug. 29, 2014  (EP) .................................... 14182869

(51) Int. Cl.
*A61B 5/145*    (2006.01)
*A61M 1/02*     (2006.01)
(Continued)

(52) U.S. Cl.
CPC ....... *A61B 5/14535* (2013.01); *A61M 1/0259* (2013.01); *A61M 1/0281* (2013.01);
(Continued)

(58) Field of Classification Search
USPC ............... 604/5.01, 6.08, 6.11, 6.15, 20, 22; 422/20, 68.1, 82.05, 73; 436/70
See application file for complete search history.

(56) References Cited

U.S. PATENT DOCUMENTS 4,479,762 A * 10/1984  Bilstad ................ A61M 1/3496
                                                    206/364
5,453,576 A *  9/1995  Krivitski .............. A61B 5/0275
                                                    600/454
(Continued)

FOREIGN PATENT DOCUMENTS

EP    1 142 598 A2   10/2001
EP    1 287 839 B1    3/2007
(Continued)

OTHER PUBLICATIONS

International Search Report and Written Opinion, counterpart PCT Appl. No. PCT/EP2015/067813, dated Oct. 15, 2015 (11 pages).

*Primary Examiner* — Dean Kwak
(74) *Attorney, Agent, or Firm* — Cook Alex Ltd.

(57) ABSTRACT

A blood processing apparatus includes a measurement device having at least one chamber element extending along a longitudinal axis and including a circumferential wall extending about the longitudinal axis, a bottom wall and a top wall together defining a flow chamber. The blood processing apparatus further includes a holder for the measurement device, the holder including a base having a reception opening for receiving the measurement device and a closure element movably arranged on the base for locking the measurement device in an inserted position in the reception opening. An ultrasonic sensor of the holder is arranged on the base. The ultrasonic sensor, in the inserted position of the measurement device, faces the bottom wall of (Continued)

the at least one chamber element, wherein the bottom wall extends transversely with respect to the longitudinal axis.

14 Claims, 8 Drawing Sheets

(51) Int. Cl.
*A61M 1/36* (2006.01)
*G01N 29/024* (2006.01)
*G01N 29/22* (2006.01)
*B01L 3/00* (2006.01)
*G01N 15/05* (2006.01)
*A61B 5/00* (2006.01)
*G01N 15/00* (2006.01)

(52) U.S. Cl.
CPC ............. *A61M 1/36* (2013.01); *A61M 1/361* (2014.02); *A61M 1/3609* (2014.02); *A61M 1/3612* (2014.02); *A61M 1/3632* (2014.02); *B01L 3/502* (2013.01); *G01N 15/05* (2013.01); *G01N 29/024* (2013.01); *G01N 29/222* (2013.01); *G01N 29/223* (2013.01); *A61B 5/4836* (2013.01); *A61B 2560/0437* (2013.01); *A61M 1/0209* (2013.01); *A61M 1/3692* (2014.02); *A61M 1/3693* (2013.01); *A61M 2205/12* (2013.01); *A61M 2205/121* (2013.01); *A61M 2205/3313* (2013.01); *A61M 2205/3368* (2013.01); *A61M 2205/3375* (2013.01); *A61M 2209/086* (2013.01); *A61M 2230/207* (2013.01); *B01L 2200/025* (2013.01); *B01L 2300/0609* (2013.01); *B01L 2300/0627* (2013.01); *B01L 2300/0848* (2013.01); *B01L 2300/0851* (2013.01); *G01N 2015/0065* (2013.01); *G01N 2015/0073* (2013.01); *G01N 2015/0092* (2013.01); *G01N 2015/055* (2013.01); *G01N 2291/02466* (2013.01); *G01N 2291/044* (2013.01)

(56) References Cited

U.S. PATENT DOCUMENTS

| | | | | |
|---|---|---|---|---|
| 5,952,560 A * | 9/1999 | Collings | ............ | G01N 29/032 73/599 |
| 5,983,120 A | 11/1999 | Groner et al. | | |
| 6,144,444 A | 11/2000 | Haworth et al. | | |
| 6,740,036 B1 * | 5/2004 | Lee | ............ | A61B 5/02042 210/739 |
| 6,806,947 B1 | 10/2004 | Ekdahl et al. | | |
| 6,849,039 B2 | 2/2005 | Min et al. | | |
| 6,875,191 B2 | 4/2005 | Smith et al. | | |
| 6,994,781 B2 | 2/2006 | Cork et al. | | |
| 7,523,649 B2 * | 4/2009 | Corey | ............ | A61B 5/14535 422/68.1 |
| 7,661,294 B2 * | 2/2010 | Dam | ............ | A61M 1/3626 250/343 |
| 7,838,296 B2 | 11/2010 | Corey et al. | | |
| 7,935,081 B2 * | 5/2011 | Flaker | ............ | A61B 5/0836 604/131 |
| 8,105,265 B2 * | 1/2012 | Demers | ............ | A61M 1/106 210/739 |
| 8,597,505 B2 * | 12/2013 | Fulkerson | ............ | B01D 61/32 210/86 |
| 9,283,315 B2 * | 3/2016 | Dam | ............ | A61B 5/14535 |
| 9,316,523 B2 * | 4/2016 | Schneider | ............ | G01F 23/268 |
| 2002/0033370 A1 * | 3/2002 | Bainbridge | ............ | A61M 1/3696 210/782 |
| 2003/0042181 A1 | 3/2003 | Metzner | | |
| 2003/0222029 A1 * | 12/2003 | Muller | ............ | A61M 1/3693 210/739 |
| 2005/0230292 A1 | 10/2005 | Beden et al. | | |
| 2006/0226057 A1 * | 10/2006 | Robinson | ............ | A61M 1/3693 210/103 |
| 2008/0025872 A1 * | 1/2008 | Dykes | ............ | A61B 5/14546 422/68.1 |
| 2010/0121170 A1 * | 5/2010 | Rule | ............ | A61B 5/1427 600/365 |
| 2011/0009800 A1 * | 1/2011 | Dam | ............ | A61M 1/3626 604/6.16 |
| 2011/0269167 A1 * | 11/2011 | Bene | ............ | A61M 1/16 435/29 |
| 2013/0317408 A1 | 11/2013 | Schade | | |
| 2016/0202237 A1 * | 7/2016 | Zeng | ............ | G01N 33/49 435/29 |

FOREIGN PATENT DOCUMENTS

| | | |
|---|---|---|
| EP | 2 666 492 A1 | 11/2013 |
| JP | H11-500648 | 1/1999 |
| JP | 2002-524211 | 8/2002 |
| JP | 2003-075304 | 3/2003 |
| JP | 2004-503756 | 2/2004 |
| JP | 2005-534346 | 11/2005 |
| JP | 2006-503650 | 2/2006 |
| JP | 2006-506607 | 2/2006 |
| JP | 2013-519077 | 5/2013 |
| WO | WO2003/101510 A1 | 12/2003 |
| WO | WO 2007/105805 | 9/2007 |

* cited by examiner

BLOOD PROCESSING APPARATUS COMPRISING A HOLDER DEVICE FOR A MEASUREMENT DEVICE

The present application is a U.S. National Stage of PCT International Patent Application No. PCT/EP2015/067813, filed Aug. 3, 2015, which claims priority to EP Application No. 14182869.9, filed Aug. 29, 2014, both of which are hereby incorporated herein by reference.

The invention relates to a blood processing apparatus according to the preamble of claim 1.

A blood processing apparatus of this kind comprises a measurement device having at least one chamber element for receiving a blood fluid. The at least one chamber element extends along a longitudinal axis and comprises a circumferential wall extending about the longitudinal axis, a bottom wall and a top wall together defining a flow chamber. The at least one chamber element further comprises an inlet port for allowing a flow of a blood fluid into the flow chamber and an outlet port for allowing a flow of a blood fluid out of the flow chamber. The blood processing apparatus furthermore comprises a holder device for holding the measurement device. The holder device comprises a base having a reception opening for receiving the measurement device and a closure element movably arranged on the base for locking the measurement device in an inserted position in the reception opening. By means of the holder device the measurement device, which for example may be part of a disposal tubing set, may be attached to a housing of the blood processing apparatus for operation of the blood processing apparatus.

The holder device comprises an ultrasonic sensor element which is arranged on the base of the holder device. The ultrasonic sensor element is adapted to produce an ultrasonic sensor signal for measuring a haematocrit value of a blood fluid in the flow chamber.

EP 1 287 839 B1 discloses a blood processing apparatus in the shape of a dialysis machine which comprises a holder chamber into which a disposable cassette may be inserted. The disposable cassette includes a chamber element having an inlet port and an outlet port for allowing a blood flow through the chamber element. On the holder chamber a temperature sensor and an ultrasonic sensor are arranged for measuring the temperature of the blood in the chamber element as well as a haematocrit value of the blood in the chamber element.

EP 2 666 492 A1 discloses a medical device for the extracorporeal blood treatment comprising a holder device into which a tube may be inserted. The holder device comprises multiple sensor units operating under different functional principles, in particular a thermal sensor element and an ultrasonic sensor element.

U.S. Pat. No. 6,144,444 discloses a holder device into which a tube may be inserted. The holder device is adapted to determine parameters of blood circulating through an extracorporeal circuit, in particular an oxygen saturation, a haemoglobin concentration and haematocrit.

It is an object of the instant invention to provide a blood processing apparatus comprising a holder device for a measurement device which allows to easily insert the measurement device into the holder device and allows for a reliable measurement of in particular a haematocrit value of a blood flow through the measurement device.

This object is achieved by means of a blood processing apparatus comprising the features of claim 1.

Accordingly, the ultrasonic sensor element, in the inserted position of the measurement device, faces the bottom wall of the at least one chamber element for transmitting the ultrasonic signal into the flow chamber through the bottom wall.

This is based on the idea to couple an ultrasonic sensor element to a bottom wall of the measurement device. The measurement device extends along the longitudinal axis, with the circumferential wall extending about the longitudinal axis. The chamber element of the measurement device may in particular have a generally cylindrical shape, with the bottom wall at its bottom and the top wall at its top. Because the ultrasonic sensor element comes to lie at the bottom wall of the chamber element when the measurement device is inserted into the holder device, the ultrasonic sensor element couples its ultrasonic sensor signal into the bottom wall and, via the bottom wall, transmits it into the flow chamber of the chamber element. The ultrasonic sensor signal, for example an ultrasonic pulse, then propagates through the flow chamber and is partially reflected at different faces of the chamber element, wherein such reflections may be recorded as echo signals by the ultrasonic sensor element and may be used to determine the haematocrit of the blood contained in the chamber element.

The closure element of the holder device, in one embodiment, is designed to, in the inserted position of the measurement device, exert a predefined force onto the at least one chamber element along the longitudinal axis. The predefined force may, for example, be larger than 15 N and serves to press the chamber element with its bottom wall against the ultrasonic sensor element such that a beneficial coupling of the ultrasonic sensor element to the bottom wall of the chamber element is achieved.

The closure element, for this, may comprise a fixing element protruding towards the inside of the reception opening and, in the inserted position of the measurement device and in a closed position of the closure element, acting onto the top wall of the chamber element such that the chamber element is pressed against the ultrasonic sensor element.

The ultrasonic sensor element, in one embodiment, comprises a coupling pad, which, in the inserted position of the measurement device, is in abutment with the bottom wall of the at least one chamber element. The coupling pad lies, in the inserted position of the measurement device, in-between the bottom wall and such components of the ultrasonic sensor element that are functional to emit and receive an ultrasonic sensor signal, in particular ultrasonic signal pulses. The coupling pad consists of a material providing a beneficial coupling of ultrasonic signals from the ultrasonic sensor element into the bottom wall and, vice versa, from the bottom wall into the ultrasonic sensor element.

The chamber element for example has a generally cylindrical shape. The bottom wall, hence, may extend transversally with respect to the longitudinal axis and the top wall may be arranged in parallel to the bottom wall and may also extend transversely with respect to the longitudinal axis. The circumferential wall extends about the longitudinal axis such that the circumferential wall, together with the bottom wall and the top wall, encloses the flow chamber contained in the chamber element.

The holder device, in one embodiment, may be constituted such that the chamber element is arranged in a tilted fashion in the reception opening of the holder device when it is inserted into the holder device (assuming an intended use and placement of the blood processing apparatus). In particular, the longitudinal axis of the chamber element, in the inserted position of the measurement device, may be arranged at a tilted angle with respect to the direction of gravity. In this case, the inlet port beneficially is arranged in vicinity of the bottom wall, and the outlet port is arranged in the vicinity of the top wall. If the outlet port is arranged at or close to the highest point of the flow chamber within the chamber element, air bubbles can rise in the flow chamber towards the outlet port and can be washed out through the outlet port in an effective manner such that they do not remain in the flow chamber. This allows for a measurement of haematocrit in the blood flowing through the flow chamber, without the measurement being disturbed by the presence of air bubbles in the flow chamber.

The longitudinal axis may be tilted with respect to the direction of gravity for example by an angle in-between 45° and 70°. In particular, the longitudinal axis may be tilted with respect to the direction of gravity by an angle of 60° (corresponding to an angle of 30° with respect to the horizontal axis).

In addition to an ultrasonic sensor element, the holder device may comprise further sensor elements for measuring further parameters of the blood flowing through the flow chamber. For example, the holder device may comprise an infrared sensor element arranged on the base and being constituted to measure a temperature of a blood flowing in the flow chamber. The infrared sensor element may be constituted to receive infrared radiation emitted from the chamber element and, from the infrared radiation, may determine a temperature of the blood inside the flow chamber.

The infrared sensor element may, in one embodiment, for example face the circumferential wall of the at least one chamber element when the measurement device is inserted in the holder device. The infrared sensor element hence is placed at the circumferential wall of the chamber element, in contrast to the ultrasonic sensor element which is arranged at the bottom wall of the chamber element.

For receiving the measurement device, the base may for example comprise a first tilted face and a second tilted face extending transversely with respect to the first tilted face. The first tilted face and the second tilted face hence describe a right angle with respect to each other. Herein, the ultrasonic sensor element is arranged on the first tilted face, whereas the infrared sensor element is arranged on the second tilted face. In the inserted position of the measurement device the bottom wall of the chamber element faces the first tilted face, whereas the circumferential wall faces the second tilted face such that the ultrasonic sensor element comes to lie at the bottom wall and the infrared sensor element comes to lie at the circumferential wall of the chamber element.

To allow for a reliable measurement of the temperature inside the flow chamber, the circumferential wall beneficially comprises a flat face at an outer side facing away from the flow chamber. The circumferential wall at its outside hence is partially flattened, wherein in the inserted position of the measurement device the flat face of the circumferential wall beneficially is in abutment with the second tilted face of the base of the holder device.

If the circumferential wall, at the flat face, comprises a reduced wall thickness as compared to other portions of the circumferential wall, it can be made sure that via the flat face a reliable temperature measurement of the temperature inside the flow chamber can be obtained. For this, infrared radiation emitted from the flat face is received by the infrared sensor element and from the infrared radiation a temperature at the flat face is determined, wherein the temperature at the flat face at least approximately will match the temperature inside the flow chamber, due to the thin wall thickness at the flat face.

In a particular embodiment, the second tilted face may comprise an infrared window for transmitting infrared radiation from the flat face to an infrared sensor element being located behind the infrared window when viewed from the measurement device. The infrared window of the tilted face may be fabricated of a material having a good transparency for infrared radiation in the relevant wavelength region such that, via the infrared window, infrared radiation is transmitted from the flat face to the infrared sensor element being located behind the infrared window.

In a particular embodiment, the measurement device may comprise two chamber elements. Herein, a first chamber element and a second chamber element may be connected to each other and hence may form an integral unit, wherein the first chamber element and the second chamber element both may have a generally cylindrical shape and may be connected to each other by means of webs extending in-between the first chamber element and the second chamber element.

In this case, the holder device beneficially comprises a first ultrasonic sensor element which in the inserted position of the measurement device faces the bottom wall of the first chamber element and a second ultrasonic sensor element which in the inserted position of the measurement device faces the bottom wall of the second chamber element. The holder device hence is adapted to conduct measurements of haematocrit in the two chamber elements.

The measurement device having two chamber elements may, for example, be used to measure a haematocrit in a blood flow flowing into the blood processing apparatus as well as in a blood flow flowing out of the blood processing apparatus. This may be used to obtain haematocrit readings of blood prior to being processed in the blood processing apparatus as well as after having been processed in the blood processing apparatus. A control of the blood processing apparatus may then take place in dependence on the different haematocrit readings (compare for example the European patent application with application number 14152634.3).

The first chamber element and the second chamber element with their longitudinal axes may in particular be arranged in parallel with respect to each other. The two ultrasonic sensor elements may in particular be arranged on the first tilted face of the base of the holder device facing the bottom walls of the two chamber elements when the measurement device is inserted into the holder device.

In addition, the holder device may comprise a first infrared sensor element which in the inserted position of the measurement device faces the circumferential wall of the first chamber element and a second infrared sensor element which in the inserted position of the measurement device faces the circumferential wall of the second chamber element. The holder device hence comprises two infrared sensor elements for measuring the temperature in the two chamber elements, wherein the two infrared sensor elements may be arranged on the second tilted face and may face flat faces on the circumferential walls of the two chamber elements for obtaining temperature readings via the flat faces of the chamber elements.

In one embodiment, the holder device may be constituted to receive the measurement device in a single position. The measurement device in this case can be inserted into the holder device only in a particular position in which it is correctly received within the holder device. By this it can be made sure that even an untrained user will correctly insert the measurement device into the holder device. For example it may be provided that the closure element can be closed only if the measurement device is inserted into the base in its correct position such that a user will immediately recognize if the measurement device has not been inserted correctly into the holder device.

The measurement device, in one embodiment, comprises a handle for manually grabbing the chamber element. A user hence may grab the measurement device at the handle and may manually insert it into the reception opening of the base of the holder device. The closure element beneficially comprises an opening through which, in the inserted position of the measurement device, the handle reaches. A user hence, through the opening of the closure element, may hold the measurement device in place within the reception opening of the holder device prior to closing the closure element such that an easy handling when inserting the measurement device into the holder device and an easy closing of the closure element for locking the measurement device in the holder device become possible.

The closure element is movable with respect to the base and may be moved from an opened position, in which the measurement device can be inserted into the base of the holder device, into a closed position, in which the measurement device is locked in the reception opening of the holder device. The closure element may for example be pivotably arranged on the base and may comprise a locking element for engaging with a corresponding locking element of the base in the closed position such that in the closed position the closure element is in positive locking engagement with the base and is fixed in its position.

Figure 1:
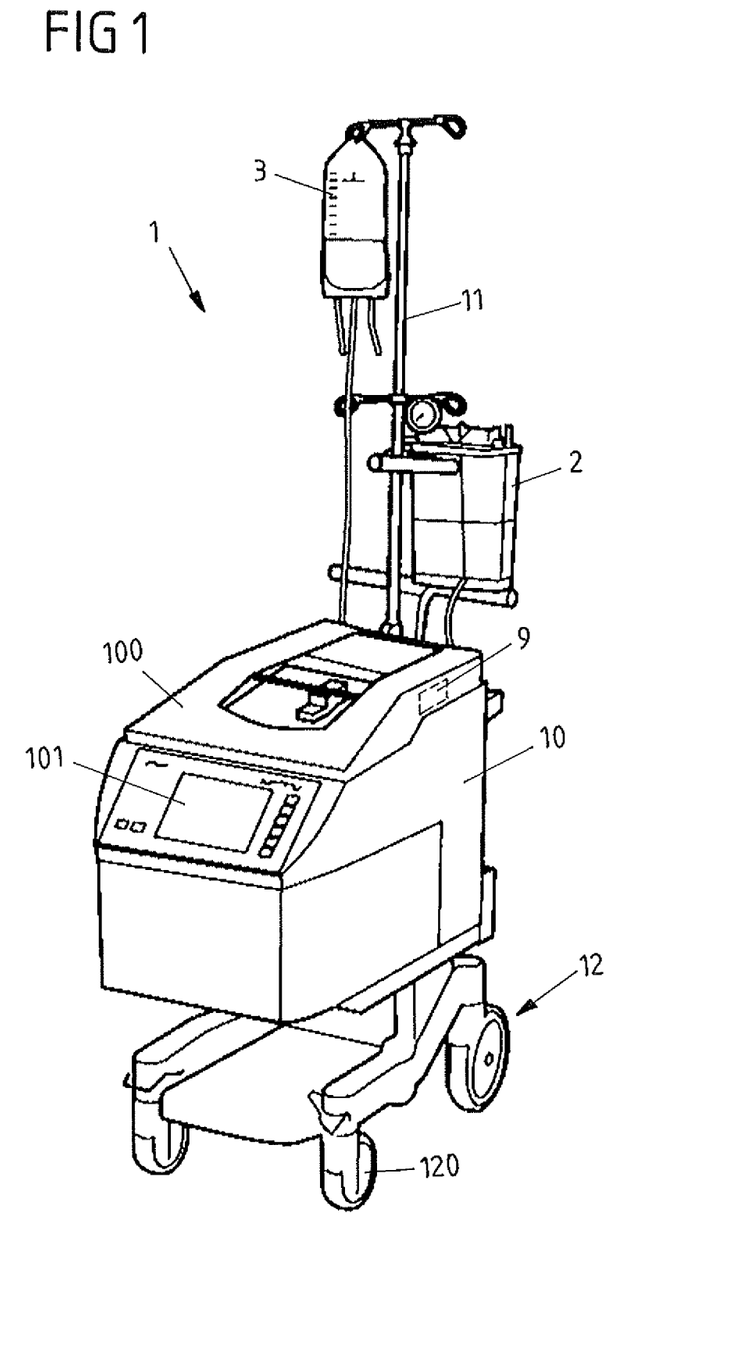
FIG. 1 shows a blood processing apparatus.

The idea underlying the invention shall subsequently be described in more detail with regard to the embodiments shown in the figures. Herein:

FIG. 1 shows a blood processing apparatus 1 which may be constituted for example as a so-called continuous autotransfusion system (CATS).

An autotransfusion system may serve to collect blood from a patient for example during or after a surgical operation. The collected blood is processed within the autotransfusion system and is recycled in order to re-transfuse it into the patient.

The blood processing apparatus 1 of FIG. 1 constituting an autotransfusion system for this purpose comprises a first reservoir container 2 for collecting blood from a patient. Through a tubing set the blood is guided from the reservoir container 2 to a washing chamber 7 (see FIGS. 2 and 3) contained in a housing 10 of the blood processing apparatus 1, by means of which the blood is processed and, after processing, collected in a second reservoir container 3 constituting a so-called re-transfusion bag, from which the blood may be re-transfused to the patient.

In the example of FIG. 1, the housing 10 comprises a lid 100 which may be opened in order to access the washing chamber 7 contained in the housing 10 and to arrange the tubing set within the housing 10 in a suitable manner. The housing 10 furthermore comprises a control panel 101 via which control commands for operating the blood processing apparatus 1 may be entered.

The housing 10 is arranged on a base 12 comprising wheels 120 such that the blood processing apparatus 1 is mobile for example in an operating theatre of a hospital.

From the housing 10 a stand 11 extends vertically on which the first reservoir container 2 for collecting the patient's blood and a second reservoir container 3 for collecting the processed blood for re-transfusing it to the patient are arranged.

On the stand 11 further containers, such as a bag for a washing solution 4 (see FIGS. 2 and 3), may be arranged.

Figure 2:
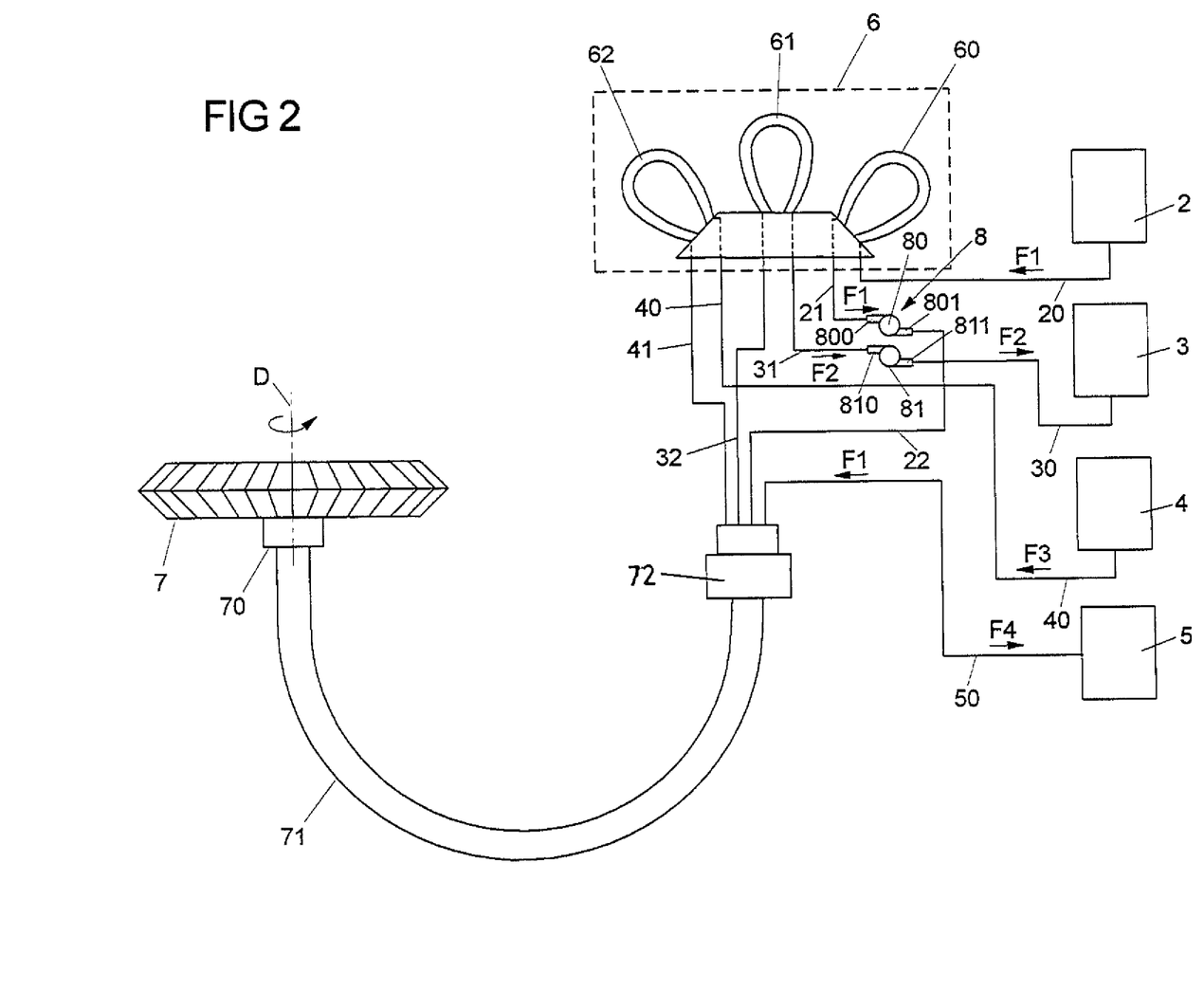
FIG. 2 shows a schematic drawing of a tubing set used with a blood processing apparatus.
Figure 3:
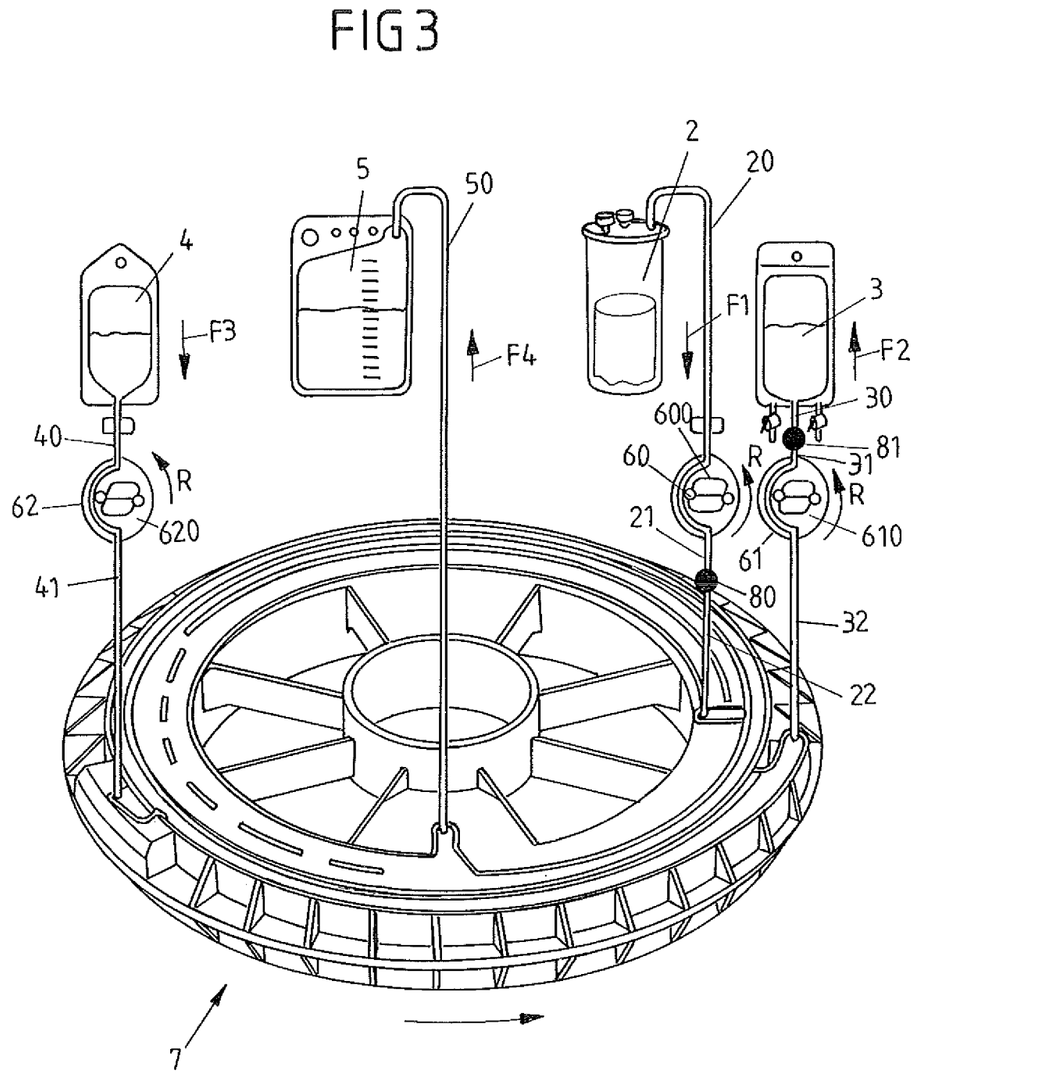
FIG. 3 shows a schematic drawing of the tubing set in relation to a washing chamber of the blood processing apparatus.

The functional setup of the blood processing apparatus 1 is as shown in FIGS. 2 and 3.

The washing chamber 7 contained in the housing 10 is rotatable about a rotational axis D and, during operation of the blood processing apparatus 1, is rotated about the rotational axis D in order to perform a centrifugation process within the washing chamber 7. The washing chamber 7 comprises a connector 70 from which a conduit 71 extends towards another connector 72.

As functionally shown in FIG. 3, the first reservoir container 2 containing blood collected from the patient, the second reservoir container 3 constituting a re-transfusion bag for re-transfusing blood to the patient, a bag for a washing solution 4, in particular a saline solution, and a waste bag 5 via a tubing set comprising different tube sections are connected to the washing chamber 7. The different tube sections herein are effectively connected at different locations on the washing chamber 7, as shown in FIG. 3.

As shown in FIG. 3, the first reservoir container 2 via a tube section 20 is connected to a tube segment 60 on which a peristaltic pump mechanism 600 acts. By means of the pump mechanism 600 a flow from the reservoir container 2 is caused through a tube section 21 via a chamber element 81 of a measurement device 8 and a tube section 22 towards the washing chamber 7.

The second reservoir container 3 is connected via a tube section 30 to a chamber element 81 of the measurement device 8 and via a tube section 31 to a tube segment 61 on which a second peristaltic pump mechanism 610 acts. The tube segment 61 via a tube section 32 is connected to the washing chamber 7.

The bag of the washing solution 4 is connected via a tube section 40 to a tube segment 62 on which a third peristaltic pump mechanism 620 acts. The tube segment 62 is connected via a tube section 41 to the washing chamber 7.

The pump mechanisms 600, 610, 620 each are constituted to perform a peristaltic pump action. For this, each pump mechanism 600, 610, 620 during operation of the blood processing apparatus 1 performs a rotational movement R and through this rotational movement R acts on the respective tube segment 60, 61, 62.

The pump mechanism 600 acting on the tube segment 60 connected to the first reservoir container 2 and likewise the pump mechanism 620 acting on the tube segment 62 connected to the bag for the washing solution 4 cause a flow in a flow direction F1, F3 towards the washing chamber 7 such that blood from the first reservoir container 2 and a washing solution from the bag 4 are transported towards the washing chamber 7.

The pump mechanism 610 acting on the tube segment 61 connected to the second reservoir container 3 for collecting processed blood for re-transfusing it to the patient, in contrast, causes a flow in a flow direction F2 from the washing chamber 7 towards the second reservoir container 3.

The waste bag 5 is connected via a tube section 50 directly to the washing chamber 7, without a pump mechanism acting on the tube section 50. During operation of the blood processing apparatus 1 a flow in a flow direction F4 from the washing chamber 7 towards the waste bag 5 is caused.

As schematically shown in FIG. 2, the tube segments 60, 61, 62, on which the three pump mechanisms 600, 610, 620 act, are arranged in a pump bed 6 in a manner known per se.

During operation of the blood processing apparatus 1 blood is transported from the reservoir container 2 into the washing chamber 7 and is processed within the washing chamber 7 in order to recycle and collect it for re-transfusion in the reservoir container 3. The processing herein takes place in the washing chamber 7 in different phases.

In a first phase—the so-called first separation phase—blood enters from the reservoir container 2 into the washing chamber 7 by pumping action of the pump mechanism 600 delivering the blood through the tube sections 20-22. In this initial separation stage, the blood is concentrated to a haematocrit value of approximately 80% within the washing chamber 7, and most of the blood plasma, cellular debris, white blood cells, platelets, anti-coagulant and other unwanted constituents are separated out and flow through the tube section 50 into the waste bag 5. This separation is effected by the rotary movement of the washing chamber 7 causing a centrifugation and, hence, a separation of the blood into its different components.

During a second phase—the so-called washing phase—the remaining constituents of the blood, in particular red blood cells, are re-suspended with a washing solution, for example a saline solution delivered from the bag for the washing solution 4 through tube sections 40, 41 by the pumping action of the pump mechanism 620. In the washing phase also a further removal of blood plasma occurs.

In a third phase—the so-called second separation phase—a final separation takes place. In this phase, the red blood cells are packed to a haematocrit value concentration of about 60 to 65%. During this phase the saline solution added during the washing phase is again removed.

The blood processed in this way leaves the washing chamber 7 through tube sections 32, 31, 30 and, by means of the pumping action of the pump mechanism 610, is pumped into the reservoir container 3 where it is collected for re-transfusion into the patient.

As shown in FIG. 2, a measurement device 8 is placed within the tubing set. The measurement device 8 serves to determine the haematocrit value in the blood flowing from the reservoir container 2 towards the washing chamber 7 and in the blood exiting the washing chamber 7 and flowing towards the reservoir container 3 for collecting the processed blood for re-transfusion. The measurement device 8 comprises two chamber elements 80, 81, each having an inlet port 800, 810 and an outlet port 801, 811.

The reservoir container 2 via its tube sections 20, 21 is connected to the inlet port 800 of the first chamber element 80, whereas the outlet port 801 of the first chamber element 80 is connected via the tube section 2 to the washing chamber 7. The washing chamber 7 in turn is connected via the tube sections 32, 31 to the inlet port 810 of the second chamber element 81, wherein the outlet port 811 of the second chamber element 81 via the tube section 30 is connected to the reservoir container 3.

As depicted in FIG. 3, the chamber elements 80, 81 of the measurement device 8 in each case are arranged downstream from the respective pump mechanism 600, 610. In particular, the pump mechanism 600 causing the flow from the reservoir container 2 towards the washing chamber 7 is arranged upstream of the inlet port 800 of the first chamber element 80. The pump mechanism 610 for delivering the processed blood into the reservoir container 3 for re-transfusing the processed blood into the patient is arranged upstream of the inlet port 810 of the second chamber element 81.

Because the chamber elements 80, 81 each are arranged downstream from the pump mechanism 600, 610, each chamber element 80, 81 is arranged on the pressure side of the respective pump mechanism 600, 610. This has the beneficial effect that cavitation effects, as they may occur upstream the pump mechanism 600, 610 due to a negative pressure created upstream by suction of the pump mechanism 600, 610, can be reduced to a minimum such that such cavitation effects do not impact measurements within the chamber elements 80, 81.

The measurement device 8 with its chamber elements 80, 81 serves to measure the haematocrit value of the blood flowing from the reservoir container 2 into the washing chamber 7 and from the washing chamber 7 into the reservoir container 3. Measuring the haematocrit value within the blood flowing from the reservoir container 2 towards the washing chamber 7 allows for controlling the process dependent on the haematocrit of the blood streaming into the washing chamber 7. Measuring the haematocrit in the processed blood flowing from the washing chamber 7 towards the reservoir container 3 provides information about the processed blood and the haematocrit obtained therein and allows for an adjustment of process parameters to obtain a desired haematocrit value.

Figure 4:
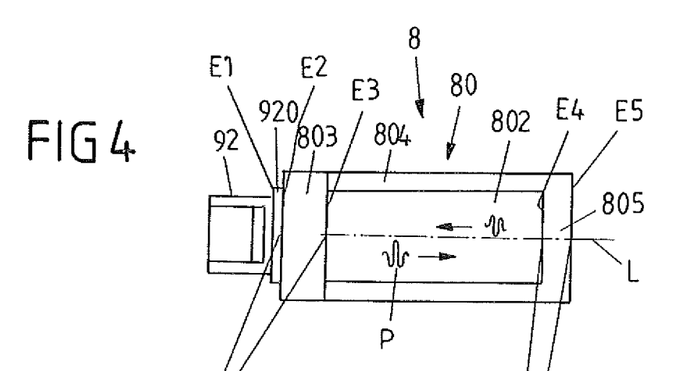
FIG. 4 shows a schematic view of a chamber element of a measurement device.
Figure 5:
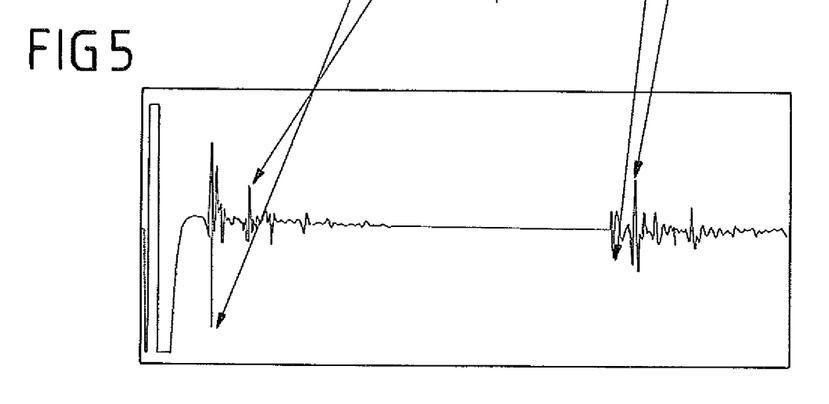
FIG. 5 shows a sensor signal received at a sensor element for measuring a haematocrit value of a blood fluid contained in the chamber element.

The measurement device 8 with its chamber elements 80, 81, as mentioned, serves to measure the haematocrit value of blood flowing through the chamber elements 80, 81. The measurement herein is carried out, as shown in FIGS. 4 and 5, by transmitting ultrasonic pulses P from an ultrasonic sensor element 92 into an associated chamber element 80, 81 and by receiving reflection signals occurring within the chamber element 80, 81. By examining the propagation times of pulses P within the chamber element 80, 81, the density of the blood contained in the chamber element 80, 81 can be analyzed and the haematocrit of the blood can be derived.

As shown in FIG. 6 and FIG. 7A to 7C, each chamber element 80, 81 has a generally cylindrical shape. Each chamber element 80, 81 comprises a bottom wall 803, 813, a circumferential wall 804, 814 and a top wall 805, 815. The bottom wall 803, 813, the circumferential wall 804, 814 and the top wall 805, 815 together define a flow chamber 802, 812 through which the blood flows.

Returning to FIG. 4, an ultrasonic sensor element 92 is arranged on the bottom wall 803 of the chamber element 80 and is coupled to the bottom wall 803 via a coupling pad 920. The ultrasonic sensor element 92 is constituted to emit ultrasonic pulses P generally along a longitudinal axis L along which the chamber element 80 with its flow chamber 802 contained therein extends.

As shown in the curve of FIG. 5, when emitting an ultrasonic pulse P into the chamber element 80, reflections occur at different faces E1-E5 of the chamber element 80.

In particular, a first reflection occurs at a face E2 in-between the coupling pad 920 and the bottom wall 803. A second reflection occurs at the face E3 of the bottom wall 803 towards the flow chamber 802. A third reflection occurs at the face E4 of the top wall 805 towards the flow chamber 802. And a fourth reflection occurs at the face E5 of the top wall 805 towards the outside.

Such reflections may be recorded in the ultrasonic sensor element 92, and from the recorded reflections the propagation times may be measured. If the geometry of the chamber element 80 is known, the densities of the materials through which the pulse P has propagated can be concluded. From the density of the blood in the flow chamber 802, then, the haematocrit value of the blood contained in the flow chamber 802 can be derived.

In order to calibrate the measurement device 8, an initial measurement may be taken by using a saline solution having a known density in order to derive the length of the different paths of the chamber element 80.

The length of the different paths in the chamber element 80 should be chosen such that reflections at the different faces E1-E5 can be discerned in a reliable manner. For this, the thickness of the bottom wall 803 and the top wall 805 and the length of the flow chamber 802 along the longitudinal axis L should be chosen appropriately.

The coupling pad 920 serves to obtain a beneficial coupling of the sensor element 92 to the bottom wall 803 of the chamber element 80. As will be described later, it may be suitable to press the chamber element 80 with its bottom wall 803 against the coupling pad 920 with a suitable force (for example exceeding 15 N).

Figure 6:
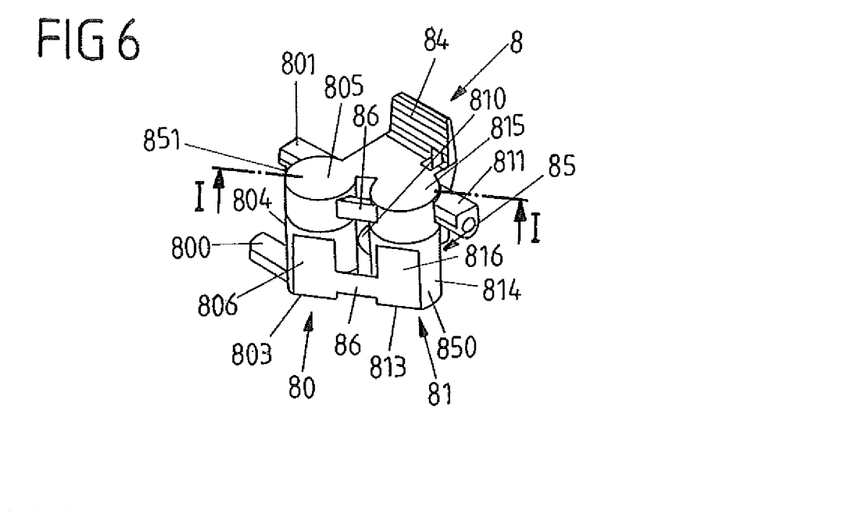
FIG. 6 shows a perspective view of an embodiment of a measurement device comprising two chamber elements.
Figure 7A:
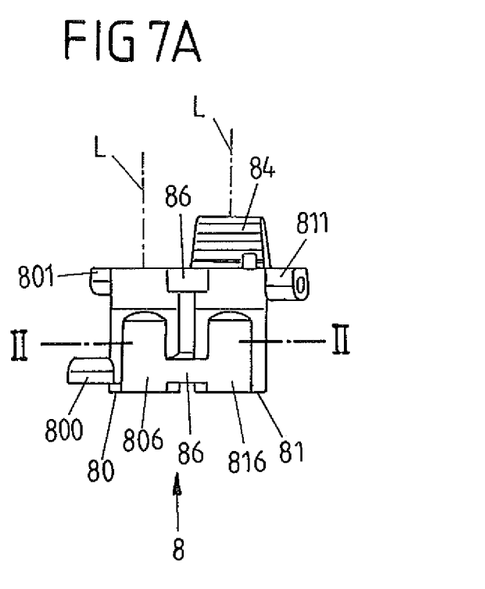
FIG. 7A shows a side view of the measurement device according to FIG. 6.
Figure 7B:
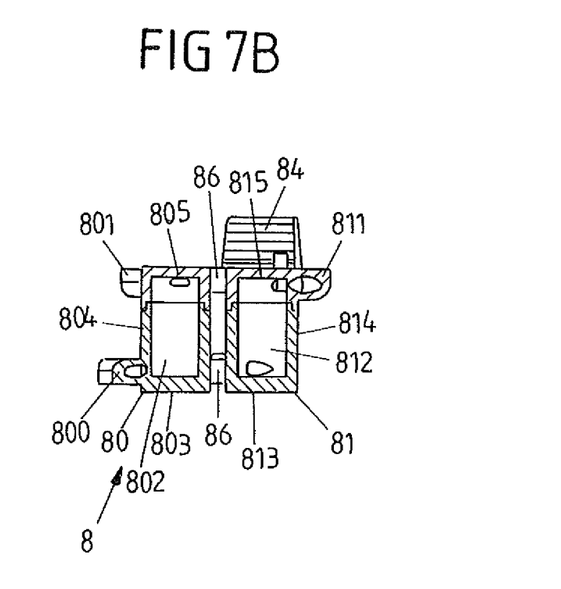
FIG. 7B shows a sectional view of the measurement device along the line I-I according to FIG. 6.
Figure 7C:
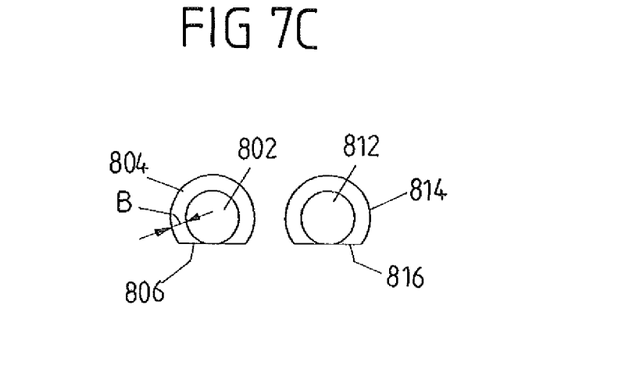
FIG. 7C shows a sectional view of the measurement device along the line Il-Il according to FIG. 7A.

FIGS. 6 and 7A, 7B show an embodiment of a measurement device 8 comprising two chamber elements 80, 81 integrally connected to each other via webs 86 to form an integral measurement unit. The measurement device 8 herein is fabricated from two housing parts 850, 851 to form a housing 85. The housing parts 850, 851 may be separately fabricated for example by injection molding from a plastics material, for example a polymer such as polycarbonate, and may subsequently be joined together to form the measurement device 8.

Each chamber element 80, 81 extends longitudinally along a longitudinal axis L. The longitudinal axes L of the chamber elements 80, 81 herein extend in parallel with respect to each other. Each chamber element 80, 81 comprises a circumferential wall 804, 814 circumferentially extending about the respective longitudinal axis L such that two generally cylindrical chamber elements 80, 81 are formed.

Each chamber element 80, 81 comprises an inlet port 800, 810 and an outlet port 801, 811. The inlet port 800, 810, in each case, is arranged in the vicinity of the bottom wall 803, 813, whereas the outlet port 801, 811 in each case is arranged in the vicinity of the top wall 805, 815.

As shown in FIG. 7B, the inlet ports 800, 810 open into the respective flow chamber 802, 812 immediately inside the bottom wall 803, 813, whereas the outlet ports 801, 811 open into the respective flow chamber immediately inside the top wall 805, 815.

As shown in FIG. 7A, the inlet port 800, 810 and the outlet port 801, 811 for each chamber element 80, 81 are arranged on the circumferential wall 804, 814 of the respective chamber element 80, 81 and are displaced with respect to each other along the longitudinal axis L. The inlet port 800, 810 and the outlet port 801, 811 hence are arranged at different heights with respect to the longitudinal axis L.

Figure 8A:
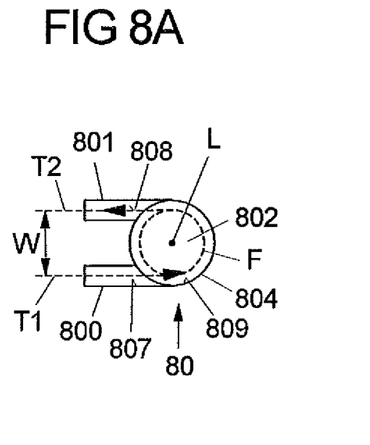
FIG. 8A shows a schematic top view of a first chamber element of the measurement device.
Figure 8B:
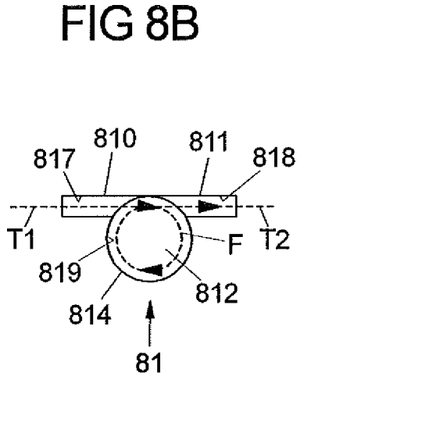
FIG. 8B shows a schematic top view of a second chamber element of the measurement device.

Furthermore, as schematically illustrated in FIG. 8A for the first chamber element 80 and in FIG. 8B for the second chamber element 81, the inlet port 800, 810 and the outlet port 801, 811 each comprise a conduit 807, 808, 817, 818 for allowing a flow into the flow chamber 802, 812 respectively out of the flow chamber 802, 812. The conduits 807, 808, 817, 818 extend along tangential axes T1, T2 which do not intersect with the longitudinal axis L and hence form skew lines with the longitudinal axis L.

In particular, the conduit 807 of the inlet port 800 of the first chamber element 80 extends along a first tangential axis T1 not intersecting with the longitudinal axis L, as shown in FIG. 8A. Likewise, the conduit 808 of the outlet port 801 of the first chamber element 80 extends along a second tangential axis T2, which runs in parallel to the first tangential axis T1 and is displaced by a displacement W from the first tangential axis T1.

For the first chamber element 80, blood flows into the flow chamber 802 in a first direction and leaves the flow chamber 802 through the outlet port 801 in an opposite, second direction. Due to the conduits 807, 808 extending along the tangential directions T1, T2, the inlet port 800 and the outlet port 801 open tangentially into the flow chamber 802 such that the flow F enters the flow chamber 802 tangentially with respect to an inner surface 809 of the flow chamber 802 and, likewise, tangentially exits the flow chamber 802 through the outlet port 801.

In combination with the displacement of the inlet port 800 and the outlet port 801 along the longitudinal axis L, this causes a turbulent flow F within the flow chamber 802, as it is illustrated in FIG. 8A. Such turbulent flow F reduces the risk for depositions within the flow chamber 802.

As shown in FIG. 8B for the second chamber element 81, the conduits 817, 818 of the inlet port 810 and the outlet port 811 of the second chamber element 81 likewise open tangentially into the flow chamber 812 to cause a turbulent flow F in the flow chamber 812. Herein, the tangential axes T1, T2 are in line with each other (when viewed from the top), but the inlet port 810 and the outlet port 811 extend towards different sides from the circumferential wall 814 of the second chamber element 81.

Figure 8C:
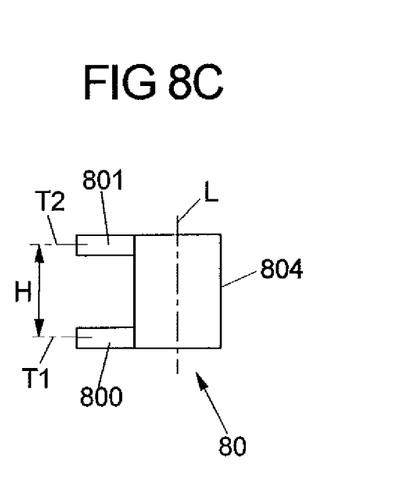
FIG. 8C shows a schematic side view of the first chamber element of the measurement device.
Figure 8D:
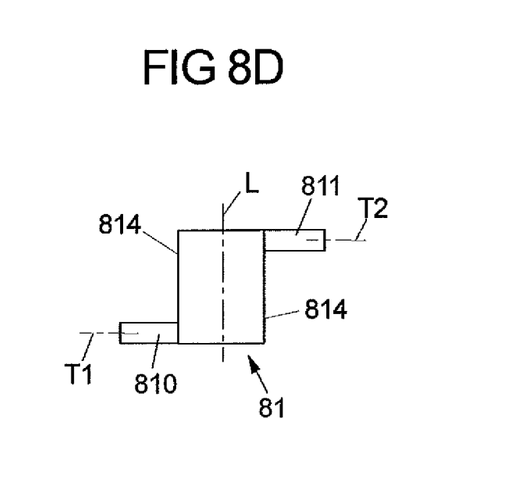
FIG. 8D shows a schematic side view of the second chamber element of the measurement device.

FIGS. 8C and 8D illustrate the longitudinal displacement of the inlet port 800, 810 and the outlet port 801, 811 for the different chamber elements 80, 81 along the respective longitudinal axis L. For both chamber elements 80, 81 the tangential axes T1, T2 along which the inlet port 800, 810 and the outlet port 801, 811 extend are displaced with respect to each other by a displacement H.

As visible from FIGS. 6 and 7A, each chamber element 80, 81 at the outside of its circumferential wall 804, 814 comprises a flat face 806, 816, the flat faces 806, 816 being aligned such that they lie in the same plane. As visible from the sectional drawing of FIG. 7C, in the region of the flat face 806, 816 the circumferential wall 804, 814 comprises a reduced wall thickness B.

The flat face 806, 816 of each chamber element 80, 81 serves for interaction with an infrared sensor element, as will be described later. Via the flat face 806, 816 the temperature inside the flow chamber 802, 812 may be measured by receiving infrared radiation emitted from the flat face 806, 816.

The measurement device 8 comprises a handle 84 for manually grabbing the measurement device 8. The handle 84 is arranged on the housing part 851 forming the top walls 805, 815 of the chamber elements 80, 81.

The measurement device 8 is part of the tubing set formed by the tube sections connecting the reservoir container 2, the reservoir container 3, the bag for the washing solution 4 and the waste bag 5 to the washing chamber 7. In particular, an autotransfusion set may be disposable and may consist of the washing chamber 7 and all tube sections for connecting the washing chamber 7 with the respective bags or containers 2-5, including the tube segments 60-62 interacting with the pump mechanisms 600-620.

The blood processing apparatus 1, as schematically shown in FIG. 1, receives in its housing 10 the washing chamber 7 and comprises a holder device 9 for receiving the measurement device 8. An embodiment of such a holder device 9 is shown in FIGS. 9 to 11.

Figure 9:
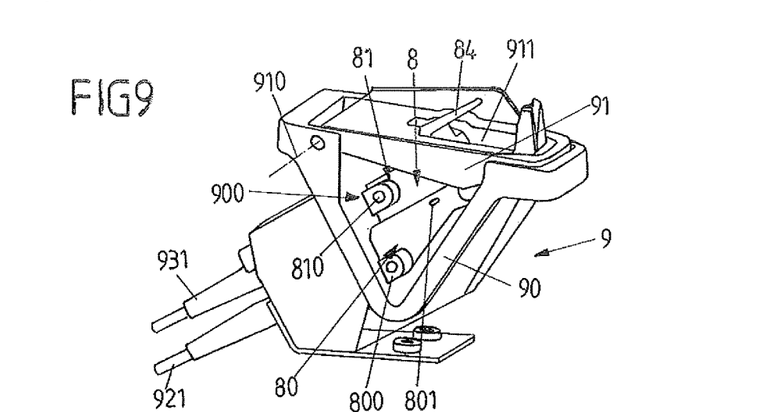
FIG. 9 shows a perspective view of a holder device of the blood processing apparatus with a measurement device received therein.
Figure 10:
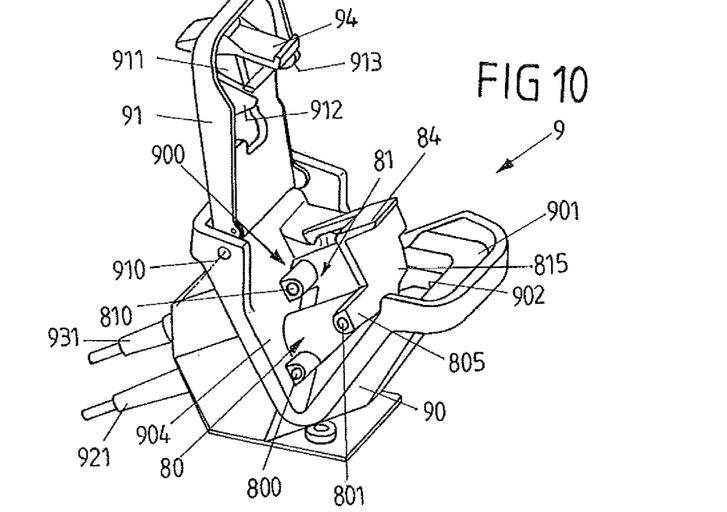
FIG. 10 shows a perspective view of the holder device with a closure element in an opened position.
Figure 11:
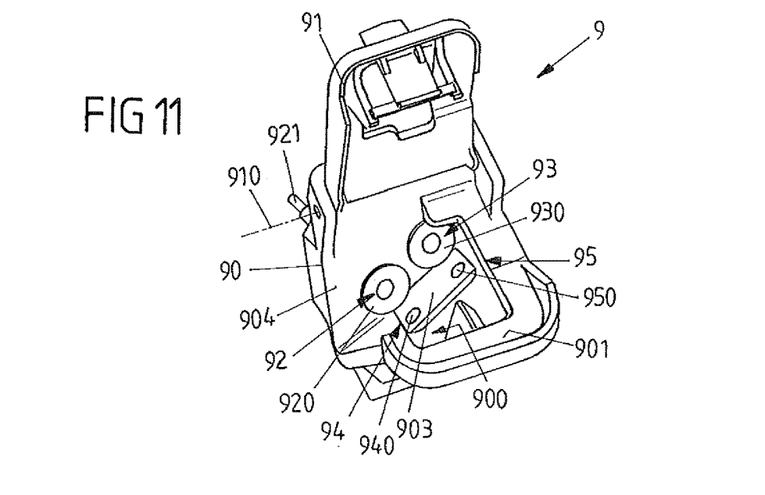
FIG. 11 shows a perspective view of the holder device, without a measurement device received therein.

The holder device 9 in the embodiment of FIGS. 9 to 11 comprises a base 90 and a closure element 91 which is arranged on the base 90 and is pivotable about a pivoting axis 910 with respect to the base 90. The base 90 forms a reception opening 900 into which the measurement device 8 with its chamber elements 80, 81 may be inserted such that, in an inserted position shown in FIGS. 9 and 10, the measurement device 8 is received in the reception opening 900.

Figure 12:
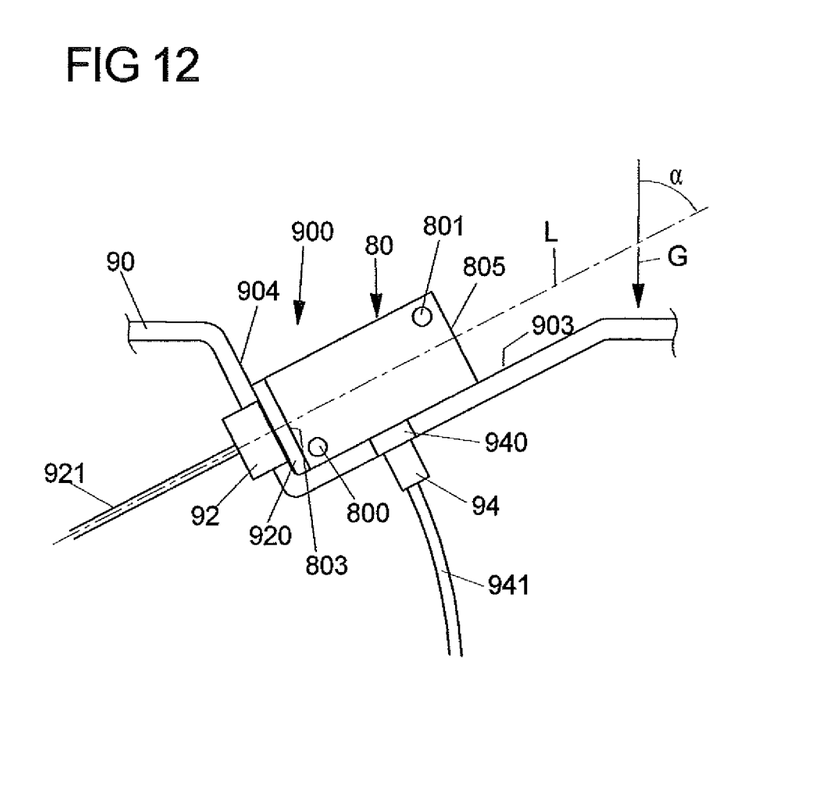
FIG. 12 shows a schematic view of the holder device in relation to a measurement device.

The base 90 comprises, as shown in FIG. 11 and as schematically illustrated in FIG. 12, a first tilted face 904 and a second tilted face 903. The tilted faces 903, 904 are arranged perpendicularly to each other and serve to abut the bottom walls 803, 813 respectively flat faces 806, 816 of the circumferential walls 804, 814 of the chamber elements 80, 81.

Herein, at the first tilted face 904 two ultrasonic sensor elements 92, 93 are arranged which comprise coupling pads 920, 930 and face with their coupling pads 920, 930 towards the outside. At the second tilted face 903 two infrared windows 940, 950 are arranged which are (at least partially) transparent for infrared radiation and form windows for infrared sensors 94, 95 located behind the infrared windows 940, 950, as schematically shown in FIG. 12.

In its inserted position the measurement device 8 with its chamber elements 80, 81 is inserted into the reception opening 900 such that the bottom walls 803, 813 of the chamber elements 80, 81 face the first tilted face 904 and are in contact with the coupling pads 920, 930. At the same time, the chamber elements 80, 81 with the flat faces 806, 816 abut the second tilted face 903 such that the flat face 806 of the first chamber element 80 faces the infrared window 940 and the flat face 816 of the second chamber element 81 faces the infrared window 950.

For inserting the measurement device 8 into the reception opening 900, the closure element 91 may be opened, as it is shown in FIGS. 10 and 11. After inserting the measurement device 8 into the reception opening 900, the closure element 91 is closed, as shown in FIG. 9, such that a front edge of the closure element 91 comes to lie at an edge section 901 of the base 90. In the closed position the closure element 91 via a locking element 914 is locked with respect to the base 90 in that the locking element 914 engages a corresponding locking element 902 of the base 90 such that a positive locking between the closure element 91 and the base 90 is achieved.

In the closed position of the closure element 91 fixing elements 912, 913 protruding from the inner face of the closure element 91 facing the inside of the reception opening 900 abut the chamber elements 80, 81 at their top walls 805, 815. By means of the fixing elements 912, 913 a force is exerted on the chamber elements 80, 81 along the longitudinal axis L such that the chamber elements 80, 81 are pressed with a predefined force against the coupling pads 920, 930 of the ultrasonic sensor elements 92, 93. In this way, a beneficial coupling of the sensor elements 92, 93 to the bottom walls 803, 813 of the chamber elements 80, 81 is achieved.

Figure 13:
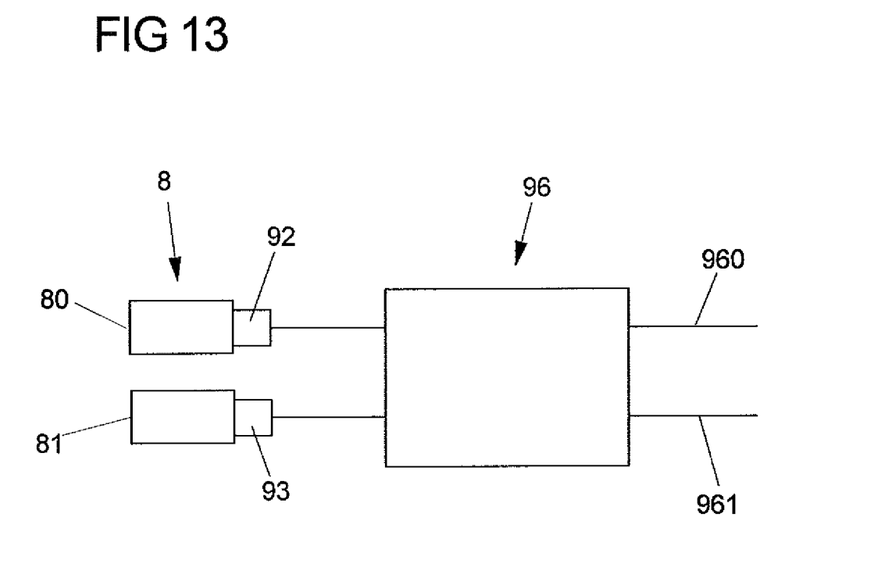
FIG. 13 shows a schematic view of a control circuit connected to ultrasonic sensor elements of the holder device.

As shown in FIGS. 9 and 10, connecting lines 921, 931 are connected to the sensor elements 92, 93 and serve to electrically connect the sensor elements 92, 93 to a control unit 96, as it is shown in FIG. 13. Via the connecting lines 921, 931 the senor elements 92, 93 are excited to produce ultrasonic pulses P, and reflection signals received at the sensor elements 92, 93 are transmitted as sensor signals to the control unit 96.

In the control unit 96 a signal processing takes place in order to determine a haematocrit value of the blood flowing through the respective chamber element 80, 81. The control unit 96 comprises a power line 960 for electrically feeding the control unit 96 and a data output line 961 for providing data to other units.

The infrared sensor elements 94, 95 are used to determine a temperature of blood in the chamber elements 80, 81. As sown in FIG. 12, each infrared sensor element 94, 95 may be connected to a connecting line 941 (shown in FIG. 12 only for the infrared sensor element 94) for transmitting sensor signals to the control unit 96.

As shown in FIG. 12, the chamber elements 80, 81 with their longitudinal axes L are arranged at an angle α with respect to the direction of gravity G. Because the outlet port 801, 811 for each chamber element 80, 81 is arranged at the top wall 805, 815 of the respective chamber element 80, 81, air bubbles within the flow chamber 802, 812 may rise in the flow chamber 802, 812 and may be washed out through the respective outlet port 801, 811 such that the air bubbles are removed from the flow chamber 802, 812. Hence, measurements within the chamber element 80, 81 are not disturbed by the presence of air bubbles.

The outlet port 801, 811 for each chamber element 80, 81, when inserted into the holder device 9, herein beneficially is arranged at the highest point of the flow chamber 802, 812 with respect to the direction of gravity G, as it is illustrated in FIG. 12. This ensures that air bubbles rising in the flow chamber 802, 812 against the direction of gravity G may exit the flow chamber 802, 812 through the outlet port 801, 811 and are not caught within the flow chamber 802, 812.

The closure element 91 comprises an opening 911 through which the handle 84 extends when the measurement device 8 is inserted into the reception opening 900 and the closure element 91 is closed, as it is shown in FIG. 9. A user hence may hold the measurement device 8 by grabbing the handle 84 until the closure element 91 is fully closed, which makes it easy to insert the measurement device 8 in a correct manner into the holder device 9.

The holder device 9 beneficially is constituted such that the measurement device 8 may be inserted into the reception opening 900 only in a single position. This ensures that the measurement device 8 is inserted correctly into the holder device 9 even by untrained users.

The idea underlying the invention is not limited to the embodiments described above, but may be used also in entirely different embodiments.

In particular, the invention is not limited to autotransfusion systems, but may be used also within other medical systems for processing blood.

LIST OF REFERENCE NUMERALS

1 Blood processing apparatus
10 Housing
100 Lid
101 Control panel
11 Stand
12 Base
120 Wheels
2 Reservoir container
20-22 Tube section
3 Re-transfusion bag
30-32 Tube section
4 Bag for washing solution
40, 41 Tube section
5 Waste bag
50 Connection tube
6 Pump bed
60-62 Tube segment
600-620 Pump mechanism
7 Washing chamber
70 Connector
71 Conduit
72 Connector
8 Measurement device
80, 81 Chamber element
800, 810 Inlet port
801, 811 Outlet port
802, 812 Flow chamber
803, 813 Bottom wall
804, 814 Circumferential wall
805, 815 Top wall
806, 816 Flat face
807, 817 Conduit
808, 818 Conduit
809, 819 Inner surface
84 Handle
85 Housing
850, 851 Housing part
86 Webs
9 Holder device
90 Base
900 Reception opening
901 Edge section
902 Locking element
903, 904 Tilted face
91 Closure element
910 Pivoting axis
911 Opening
912, 913 Fixing element
914 Locking element
92, 93 Ultrasonic sensor element
920, 930 Coupling pad
921, 931 Connecting line
94, 95 Infrared sensor element
940, 950 Infrared window
941, 951 Connection
96 Control unit
960, 961 Connections
α Angle
B Wall thickness
D Rotational axis
E1-E5 Face
F Flow
F1-F4 Flow direction
G Direction of gravity
H Height
L Longitudinal axis
P Pulse
R Rotational movement
T1, T2 Tangential axis
W Width

The invention claimed is:

1. A blood processing apparatus, comprising:
a measurement device having at least one chamber element for receiving a blood fluid, wherein the at least one chamber element extends along a longitudinal axis and comprises a circumferential wall extending about the longitudinal axis, a bottom wall and a top wall together defining a flow chamber, the at last one chamber element further comprising an inlet port for allowing a flow of a blood fluid into the flow chamber and an outlet port for allowing a flow of a blood fluid out of the flow chamber,
a holder device for holding the measurement device, the holder device comprising a base having a reception opening for receiving the measurement device and a closure element movably arranged on the base for locking the measurement device in an inserted position in the reception opening, and
an ultrasonic sensor of the holder device arranged on the base,
wherein the ultrasonic sensor, in the inserted position of the measurement device, is directed along the longitudinal axis of the at least one chamber element and faces the bottom wall of the at least one chamber element to transmit an ultrasonic signal into the flow chamber through the bottom wall, wherein the bottom wall extends transversely with respect to the longitudinal axis.

2. The blood processing apparatus according to claim 1, wherein the closure element is designed to, in the inserted position of the measurement device, exert a predefined force onto the at least one chamber element along the longitudinal axis such that the at least one chamber element with its bottom wall is pressed against the ultrasonic sensor.

3. The blood processing apparatus according to claim 1, wherein the ultrasonic sensor comprises a coupling pad which, in the inserted position of the measurement device, is in abutment with the bottom wall of the at least one chamber element.

4. The blood processing apparatus according to claim 1, wherein the longitudinal axis, in the inserted position of the measurement device, is arranged at a tilted angle with respect to the direction of gravity.

5. The blood processing apparatus according to claim 1, wherein the holder device comprises an infrared sensor arranged on the base, the infrared sensor, in the inserted position of the measurement device, facing the circumferential wall of the at least one chamber element.

6. The blood processing apparatus according to claim 5, wherein the base comprises a first tilted face and a second tilted face extending transversely with respect to the first tilted face, wherein the ultrasonic sensor is arranged on the first tilted face and the infrared sensor is arranged on the second tilted face.

7. The blood processing apparatus according to claim 6, wherein the circumferential wall of the at least one chamber element at an outer side facing away from the flow chamber comprises a flat face which, in the inserted position of the measurement device, is in abutment with the second tilted face.

8. The blood processing apparatus according to claim 7, wherein the circumferential wall, at the flat face, comprises a reduced wall thickness as compared to at least one other portion of the circumferential wall.

9. The blood processing apparatus according to claim 6, wherein the second tilted face comprises an infrared window to transmit infrared radiation, the infrared sensor being located, when viewed from the measurement device, behind the infrared window.

10. The blood processing apparatus according to claim 1, wherein the measurement device comprises a first chamber element and a second chamber element connected to each other, wherein the holder device comprises a first ultrasonic sensor which in the inserted position of the measurement device faces the bottom wall of the first chamber element and a second ultrasonic sensor which in the inserted position of the measurement device faces the bottom wall of the second chamber element.

11. The blood processing apparatus according to claim 10, wherein the holder device comprises a first infrared sensor which in the inserted position of the measurement device faces the circumferential wall of the first chamber element and a second infrared sensor which in the inserted position of the measurement device faces the circumferential wall of the second chamber element.

12. The blood processing apparatus according to claim 1, wherein the holder device is adapted to receive the measurement device in a single position.

13. The blood processing apparatus according to claim 1, wherein the measurement device comprises a handle for manually grabbing the chamber element.

14. The blood processing apparatus according to claim 13, wherein the closure element comprises an opening through which, in the inserted position of the measurement device, the handle reaches.

\* \* \* \* \*